(12) United States Patent
Sakai et al.

(10) Patent No.: US 6,333,046 B1
(45) Date of Patent: Dec. 25, 2001

(54) TRANSMUCOUS ABSORPTION ENHANCER

(75) Inventors: Michinori Sakai; Hiroshi Ohtake; Hidekazu Azuma, all of Ibaraki; Masaki Otagiri; Teruko Imai, both of Kumamoto, all of (JP)

(73) Assignee: Hisamitsu Pharmaceutical Co., Inc., Saga (JP)

( * ) Notice: Subject to any disclaimer, the term of this patent is extended or adjusted under 35 U.S.C. 154(b) by 0 days.

(21) Appl. No.: 09/623,386

(22) PCT Filed: Feb. 26, 1999

(86) PCT No.: PCT/JP99/00923

§ 371 Date: Nov. 27, 2000

§ 102(e) Date: Nov. 27, 2000

(87) PCT Pub. No.: WO99/44641

PCT Pub. Date: Sep. 10, 1999

(30) Foreign Application Priority Data

Mar. 2, 1998 (JP) ................................. 10-049890

(51) Int. Cl.⁷ ................ A61F 13/00; A61F 9/02

(52) U.S. Cl. .................. 424/434; 424/435; 424/436; 424/422

(58) Field of Search ................... 424/434, 422, 424/435, 436

(56) References Cited

U.S. PATENT DOCUMENTS

| 4,835,142 | * | 5/1989 | Suzuki et al. ........................ 514/53 |
| 4,952,560 | * | 8/1990 | Kigasawa et al. .................... 514/2 |
| 5,182,258 | * | 1/1993 | Chiou .................................. 514/3 |
| 5,578,567 | * | 11/1996 | Cardinaux et al. ................. 514/12 |

* cited by examiner

Primary Examiner—Thurman K. Page
Assistant Examiner—Rachel M. Bennett
(74) Attorney, Agent, or Firm—Wenderoth, Lind & Ponack, L.L.P.

(57) ABSTRACT

To provide a transmucous absorption enhancer comprising a medium-chain fatty acid salts or a bile acid salt and a glycyrrhizic acid salts capable of sustaining the effect of the absorption enhancer and allowing an agent (especially a physiologically active peptide) to be absorbed via a mucosa (especially a large intestine mucosa).

6 Claims, 13 Drawing Sheets

TRANSMUCOUS ABSORPTION ENHANCER

This application is a 371 application of PCT/JP99/00923 filed Feb. 26, 1999.

FIELD OF THE INVENTION

The present invention relates to a transmucous absorption enhancer. More particularly, this invention relates to a transmucous absorption enhancer for promoting an absorption of a physiologically active agent via a mucosa of an intestinal tract and rectal, vaginal, nasal and oral cavities and the like. Specifically, the invention relates to a transmucous absorption enhancer having a sustained effect and an absorption-promoting effect which was obtained by combining a glycyrrhizic acid salts which is used as a therapeutic agent against a chronic hepatitis, an allergic injury, an inflammation and a gastric ulcer and also as an agent for promoting an absorption via a nasal mucosa but exhibits no absorption-promoting effect in a cultured cell assay system with a medium-chain fatty acid salts or a bile acid salt, and also by specifying the amounts to be combined.

DESCRIPTION OF THE RELATED ART

A conventional oral formulation undergoes a disintegration and a dissolution generally before it reaches a large intestine after being taken orally. As a result, a physiologically active polypeptide which is degraded readily in a gastrointestinal tract can not exert a pharmacological effect reliably after an oral intake. Accordingly, such physiologically active peptide has conventionally been developed in a dosage form of a nasal, vaginal or rectal formulation of a physiologically active peptide. However, such dosage form can not be used conveniently, and a dosage form for an oral administration is still desired.

In order to formulate a physiologically active polypeptide into a dosage form for an oral administration, it is required that such polypeptide is not degraded in a gastrointestinal tract. On the other hand, a large intestine is a hopeful candidate of an absorption site of a peptide agent since it has a lower protease activity when compared with a small intestine. Nevertheless, a large intestine has a finer interstice of the cells when compared with a small intestine, due to which it usually involves a difficulty in absorbing a highly hydrophilic peptide agent. Accordingly, various attempts have been made to improve the absorption via a mucosa of a large intestine, including a method using a absorption enhancer. A absorption enhancer is employed widely in a nasal, vaginal or rectal formulation or in an oral formulation for the purpose of promoting a transmucous absorption. Examples of such absorption enhancer which have been reported are a bile acid salt having a surfactant property (JP-A-59-130820), an ionic or non-ionic surfactant (JP-A-4-247034), as well as a substance which promotes the absorption via a nasal or rectal mucosa, such as a chelating agent, a medium-chain fatty acid salts (U.S. Pat. No. 4,476,116), an alkaline metal glycyrrhizinate (JP-A-2-42027), and the like.

On the other hand, one of the assay systems for evaluating the absorption of an agent via an intestinal tract is a method using a Caco-2 cell which is a human large intestine cancer-derived cell line. When a Caco-2 cell is cultured as a monolayer for about 3 weeks on a double-chambered porous polycarbonate membrane, it exhibits a morphological and biochemical polarity of a membrane such as the formation of a villus or a tight connection, and thus is known to be a cell line capable of being used for evaluating the absorption of an agent in an intestinal tract (Hidalgo, I.J. et al., Gastroenterology, 96:736–749, 1989). Once a tight connection is formed to make a cell interstice finer, a transepitherial electrical resistance (TEER) is established between the top and the bottom of a cell monolayer, and a Caco-2 cell has a stronger intercellular connection and an extremely lower permeation through an interstice when forming such tight connection than when present as an in vivo intestine. It is also known that the results of a study on a drug permeability using a Caco-2 cell are correlated highly with the results of an in vivo study (Yamashita,setal., Pharm. Res. 14 (4) :486–491, 1997). Due to the reasons described above, a Caco-2 cell is used widely as a mean for performing an in vitro investigation of an effect of a absorption enhancer f or promoting absorption by dilating the interstice of the cells (Tomita, Metal., Pharm. Res., 5:341–346, 1980, Sawada, T et al., Pharm. Res., 8:1365–1371, 1991).

SUMMARY OF THE INVENTION

While a large number of studies have been made for developing a absorption enhancer, a substantial use has not actually been made, since a conventional absorption enhancer has an only insufficiently sustained effect.

Thus, an objective of the present invention is to provide a transmucous absorption enhancer capable of sustaining the effect of the absorption enhancer and allowing an agent (especially a physiologically active peptide) to be absorbed more efficiently via a mucosa (especially a large intestine mucosa).

Accordingly, in order to achieve the objectives described above, as the first aspect of the invention, a transmucous absorption enhancer comprising a medium-chain fatty acid salts and a glycyrrhizic acid salts is provided. In a preferred embodiment, the ratio of said medium-chain fatty acid salts and said glycyrrhizic acid salts is 1:2 to 1:100.

As the second aspect of the invention, a transmucous absorption enhancer comprising a bile acid salts and a glycyrrhizic acid salts is provided. In a preferred embodiment, the ratio of said bile acid salts and said glycyrrhizic acid salts is 1:1 to 1:100.

Preferably, in any of the aspects of the invention, said glycyrrhizic acid salts is a monoammonium glycyrrhizinate or an alkaline metal glycyrrhizinate (e.g., dipotassium or sodium salt, tripotassium or sodium salt), said medium-chain fatty acid salts is an alkaline metal salt of capric acid, caprylic acid and caproic acid (e.g., sodium or potassium salt), and said bile acid salt is sodium cholate, sodium glycocholate, sodium taurocholate, sodium deoxycholate or sodium cenodeoxycholate.

DESCRIPTION OF THE PREFERRED EMBODIMENT

Figure 1:
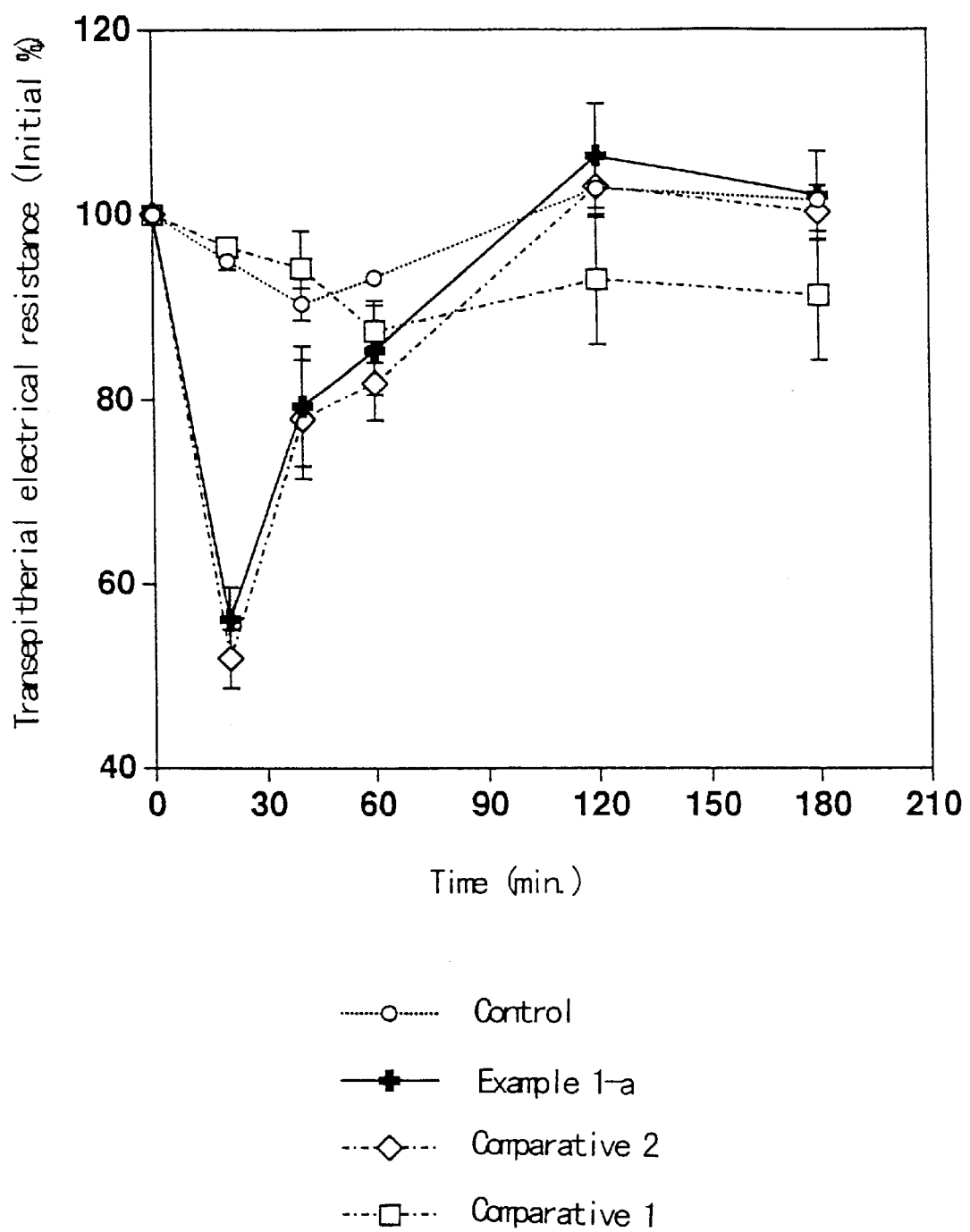
FIG. 1 is a graph showing the absorption-promoting effect of a solution of sodium caprate and sodium deoxycholate.

As described above, the present invention is established based on the findings that when a Caco-2 epithelium which is a cell line derived from a human large intestine cancer epithelium obtained as a result of our investigation for the purpose of achieving the objectives described above is used in the screening of existing absorption enhancers the effect of a conventional absorption enhancer, such as a medium-chain fatty acid salts, e.g., an alkaline metal (sodium or potassium) caprate, caprylate and capronate or a bile acid salt, e.g., sodium cholate, sodium glycocholate, sodium taurocholate, sodium deoxycholate and sodium cenodeoxycholate is sustained and enhanced by combining a certain amount of a substance which exhibits no absorption-promoting effect by itself in this cultured cell assay system such as a glycyrrhizic acid salts e.g., monoammonium glycyrrhizinate or an alkaline metal (e. g., dipotassium or sodium, tripotassium or sodium) glycyrrhizinate. More typically, the present invention provides a sustained absorption enhancer for a transmucous formulation using a certain ratio of dipotassium glycyrrhizinate as a glycyrrhizic acid salts and sodium caprate as a medium-chain fatty acid salts or sodium deoxycholate as a bile acid salt.

An inventive transmucous absorption enhancer may be formulated into a dosage form for an oral administration by being combined with a pharmacologically active substance.

Such pharmacologically active substance is not particularly limited as long as it is an effective substance when absorbed transmucosally, and may for example be peptide and a protein agents such as somatostatin, insulin, angiotensin, gastrin, pentagastrin, glucagon, calcitonin, CGRP (calcitonin gene-related peptide), EGF (epithelium growth factor), α-hANP (α-human atrial natriuretic peptide), GM-CSF (granulocyte macrophage colony stimulating factor), G-CSF (granulocyte colony stimulating factor), t-PA (tissue plasminogen activator), TNF (tumor necrosis factor), TCGF (T-cell growth factor), hGF (human growth factor), ACTH (adrenal cortex stimulating hormone), MSH (melanocyte stimulating hormone), LH (lutenizing hormone), LH-RH (lutenizing hormone-releasing hormone), encephalin, endorphin, muramyl dipeptide, neurotensin, interleukins, interferons, EPO (erythropoietin) urokinase, neocalcinostatin, oxytocin, thyroidal hormone, TRH (thyroid stimulating hormone releasing hormone), PTH (parathyroidal hormone), desmopressin, vasopressin, vasoactive intestinal peptide, cholecystokinin, bradykinin, immunogloburin, and digestion products or derivatives thereof, various allergens and digestion products or derivatives thereof.

An inventive transmucous absorption enhancer may also be formulated into a dosage form by combining a pharmacologically active substance listed above with an excipient, a binder and/or a disintegrant.

Such excipient may for example be a saccharide such as lactose, sucrose and glucose, a starch such as potato starch, wheat starch and corn starch, a cellulose such as crystalline cellulose, an inorganic salt such as anhydrous calcium phosphate and calcium carbonate, and the like.

A binder may for example be a crystalline cellulose, pullulan, gum arabic, sodium alginate, polyvinylpyrrolidone, macrogol and the like.

A disintegrant may for example be a customary inert substance for a pharmaceutical, such as carboxymethyl cellulose, calcium carboxymethyl cellulose, hydroxypropyl cellulose, hydroxypropyl starch, starch, sodium alginate and the like.

The dosage form having a composition described above may for example be a tablet, a capsule, a granule and the like, and may be used as a absorption enhancer for a formulation to be administered also to a mucosa other than a large intestinal mucosa, including nasal, oral, rectal, vaginal, pulmonary and ophthalmic mucosas. Also by employing a formulation degraded in a large intestine concomitantly, a reduction in or a loss of, or an individual variation in the bioavailability, which is often experienced with a formulation applied to a lower digestive tract, can be improved. Examples An inventive transmucous absorption enhancer is described further in detail in the following Examples, Experiments, and Comparatives, which are not intended to restrict the invention.

EXAMPLE 1

Dipotassium glycyrrhizinate (ALPS Pharmaceutical Ind. Co., LTD), sodium caprate (TOKYOKASEIKOGYO) and sodium deoxycholate (Sigma) in the amounts specified in Table 1 were mixed with a buffer solution (Hanks' balanced salt solution/calcium, magnesium free (HBSS/CMF): Biowhittaker) to prepare a absorption enhancer.

TABLE 1

| | Sodium deoxycholate | Sodium caprate | Dipotassium glycyrrhizinate |
| --- | --- | --- | --- |
| Control | 0 | 0 | 0 |
| Example 1-a | 0.02% | 0.1% | — |
| Example 1-b | — | 0.1% | 0.2% |
| Example 1-c | 0.02% | — | 0.2% |

Each absorption enhancer was dissolved in a buffer solution (Hanks' balanced salt solution/calcium, magnesium free (HBSS/CMF): Biowhittaker) just before use.

Experiment 1

Each absorption enhancer prepared in Example 1 was examined for the effect on the TEER of a Caco-2 cell.

A Caco-2 cell, after subcultured over 75 to 86 passages, was incubated in a culture flask containing a fetal calf serum (FCS)-supplemented Dulbecco's modified EAGLE medium (DMEM) at 37° C. under 95% air/5% $CO_2$. The culture medium was replace with afresh one every other day. The subculture was conducted every week using 0.25% trypsin/0.02% ethylene diamine tetracetic acid (EDTA). The cell was subjected to the experiment after incubating on a filter for 3 to 4 weeks followed by ensuring a sufficient transepitherial electric resistance (TEER)

The TEER between the top and the bottom of a Caco-2 monolayer was determined at a certain time interval using a Millicell-ERS (Millipore). One hour before initiating the experiment, only the side of the top was replaced with HBSS/CMF and allowed to stand with warming. After allowing to stand with warming, a absorption enhancer-supplemented HBSS/CMF was poured only onto the side of the top, whereby initiating the experiment. Twenty minutes after the initiation, the absorption enhancer was removed and washed once thoroughly with HBSS/CMF, and then HBSS/CMF was added again. As a comparative, a buffer solution of each compound having a composition shown in Table 2 was prepared and compared as appropriate.

TABLE 2

|  | Sodium deoxycholate | Sodium caprate | Dipotassium glycyrrhizinate | Sodium dodecylsulfate |
| --- | --- | --- | --- | --- |
| Comparative 1 | 0.02% | — | — | — |
| Comparative 2 | — | 0.1% | — | — |
| Comparative 3 | — | — | 0.2% | — |
| Comparative 4 | — | — | 0.1% | — |
| Comparative 5 | — | — | 2% | — |
| Comparative 6 | — | — | 0.02% | — |
| Comparative 7 | — | — | 1% | — |
| Comparative 8 | — | — | — | 0.2% |

Figure 2:
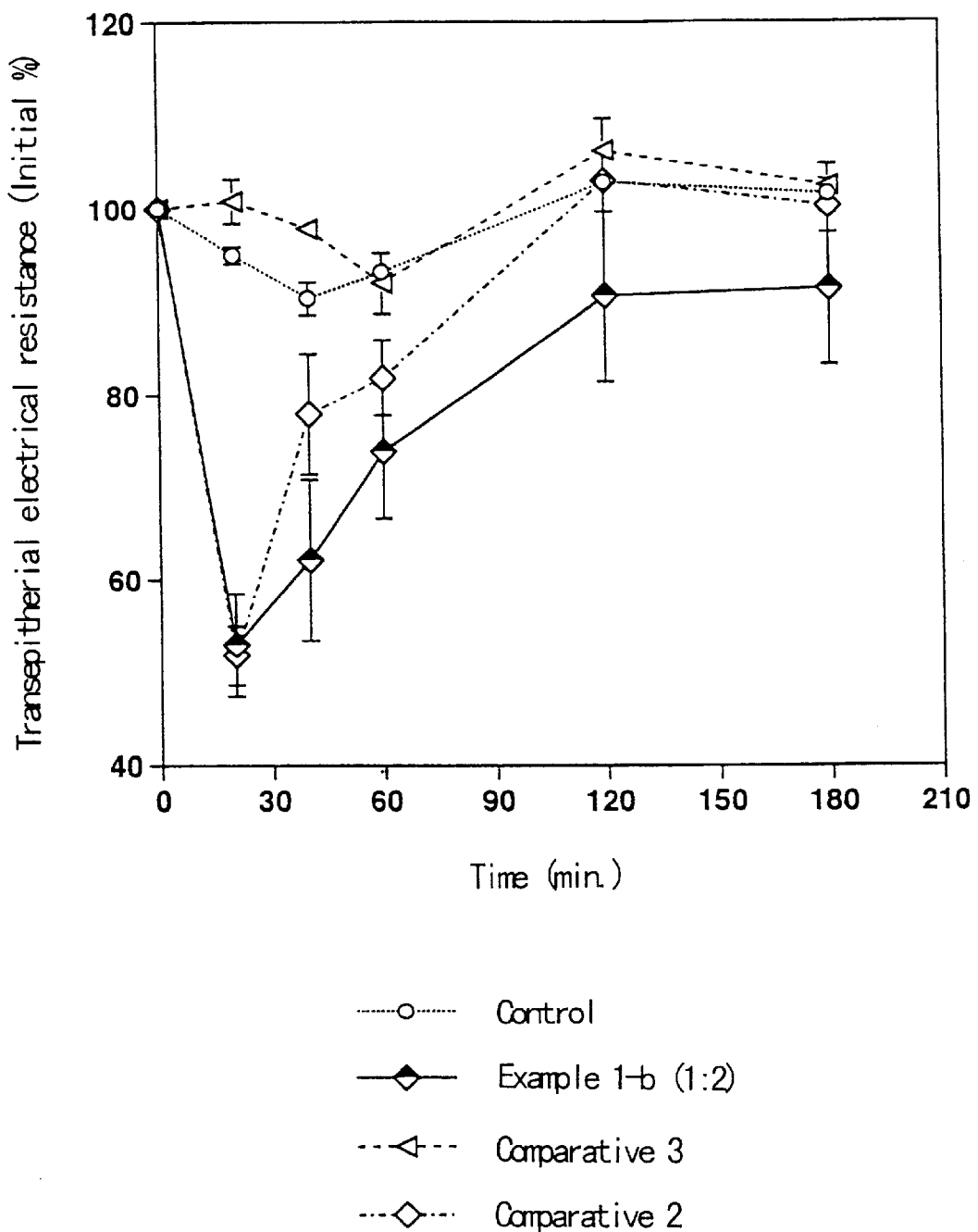
FIG. 2 is a graph showing the absorption-promoting effect of a solution of sodium caprate and dipotassium glycyrrhizinate.
Figure 3:
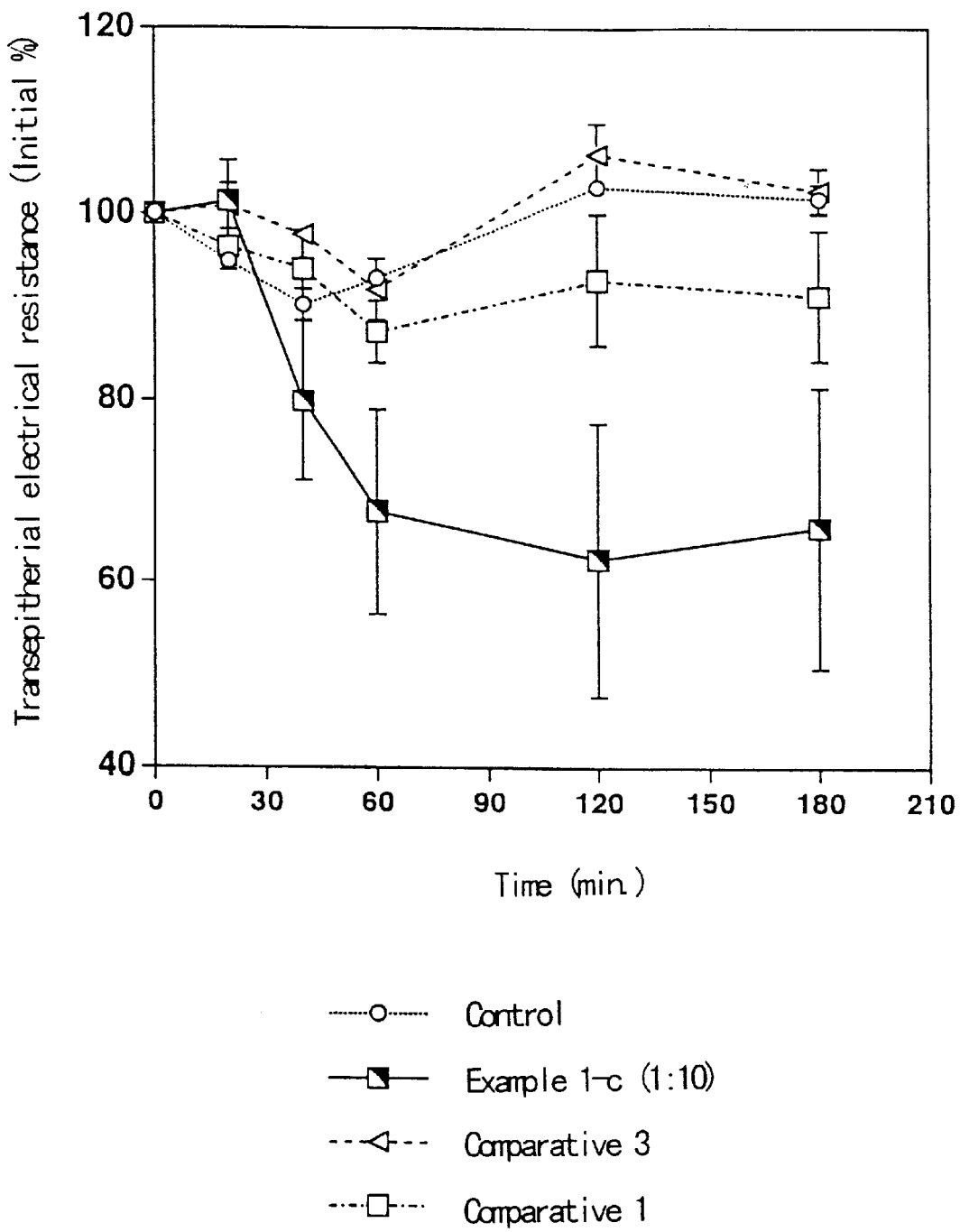
FIG. 3 is a graph showing the absorption-promoting effect of a solution of sodium deoxycholate and dipotassium glycyrrhizinate.

The results are shown in FIGS. 1 to 3. As shown in FIGS. 1 to 3, sodium caprate combined with sodium deoxycholate exhibited no clear effect (FIG. 1), but dipotassium glycyrrhizinate combined with other components exhibited a sustained effect (dipotassium glycyrrhizinate combined with sodium caprate; FIG. 2) or an enhanced effect (dipotassium glycyrrhizinate combined with sodium deoxycholate; FIG. 3).

EXAMPLE 2

Absorption enhancers having the compositions shown in Table 3 were prepared.

TABLE 3

|  | Sodium deoxycholate | Sodium caprate | Dipotassium glycyrrhizinate |
| --- | --- | --- | --- |
| Control | 0 | 0 | 0 |
| Example 2-a | — | 0.1% | 0.1% |
| Example 2-b | — | 0.1% | 1% |
| Example 2-c | — | 0.1% | 2% |
| Example 2-d | 0.02% | — | 0.02% |
| Example 2-e | 0.02% | — | 1% |
| Example 2-f | 0.02% | — | 2% |

Experiment 2

Each absorption enhancer prepared in Example 2 was examined similarly to Experiment 1.

Figure 4:
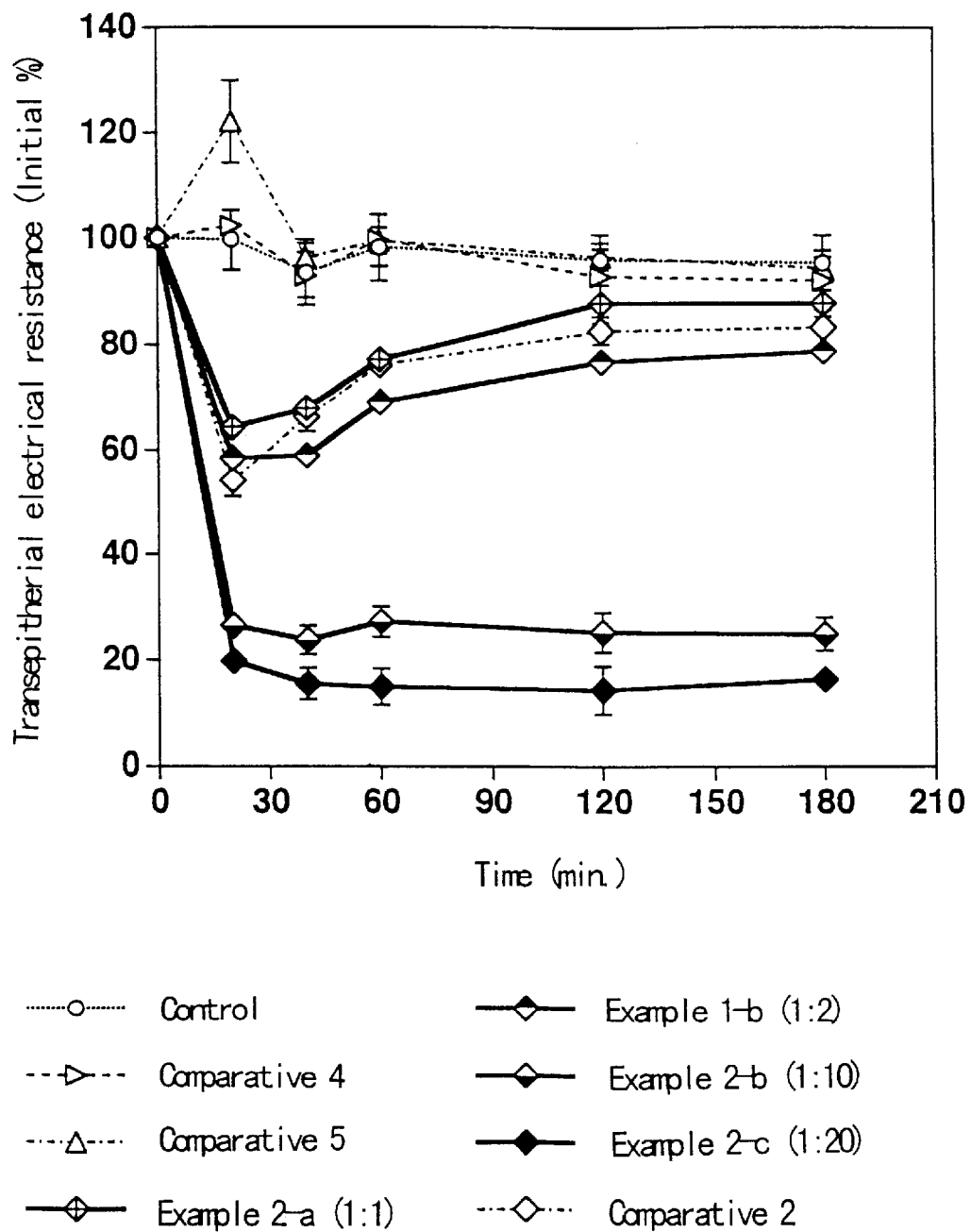
FIG. 4 is a graph showing the most effective ratio of dipotassium glycyrrhizinate and sodium caprate.
Figure 5:
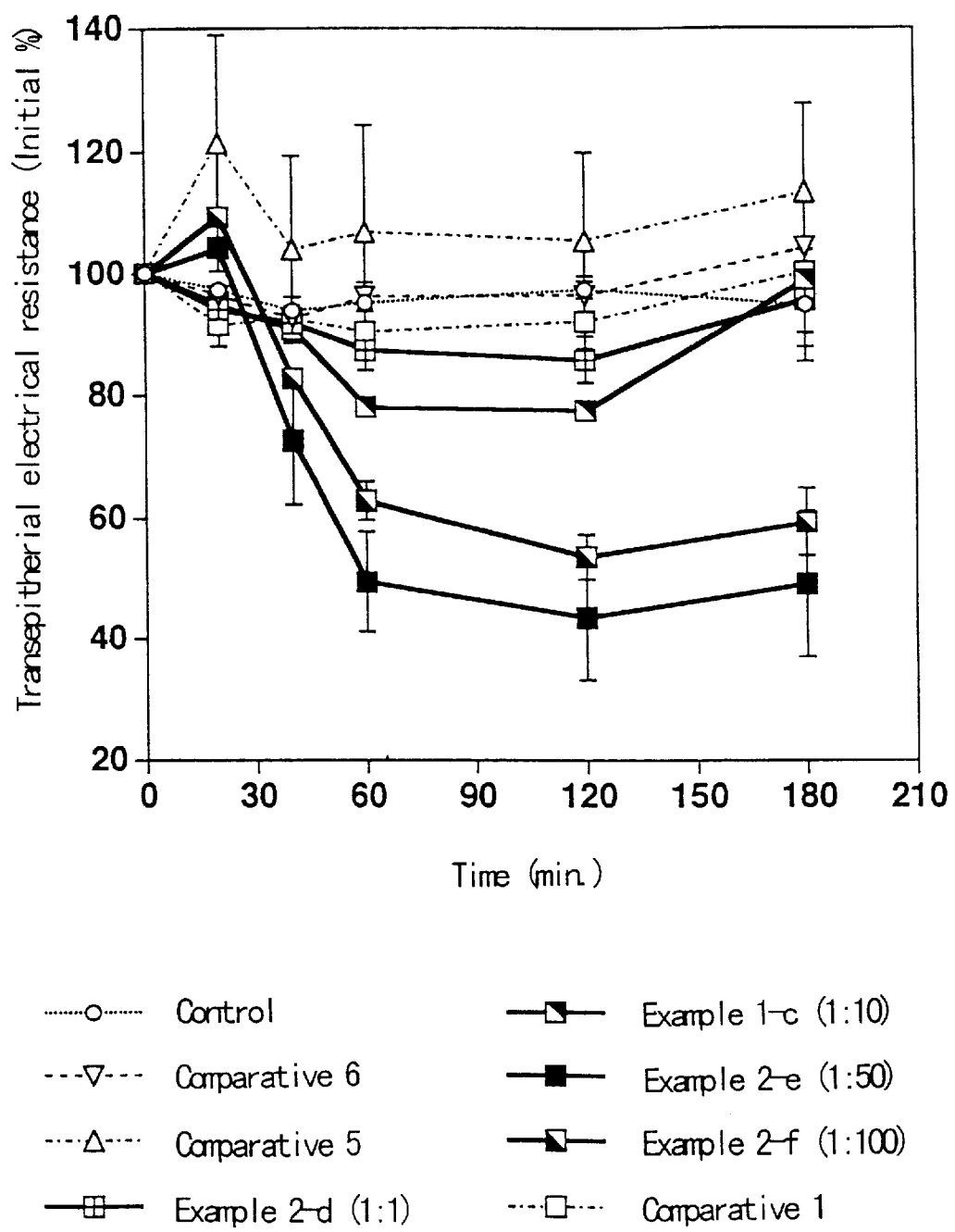
FIG. 5 is a graph showing the most effective ratio of dipotassium glycyrrhizinate and sodium deoxycholate.

The results are shown in FIG. 4 and FIG. 5. As shown in FIG. 4, an experiment in which the ratio of the two components was varied by varying the concentration of dipotassium glycyrrhizinate revealed that a higher % dipotassium glycyrrhizinate gave a more sustained effect. In this assay system, a combination of sodium caprate and dipotassium glycyrrhizinate gave an enhanced and sustained effect at the ratio of 1:2 to 1:20, with the ratio of 1:20 (Example 2-c) being the most effective. Further ratios, 1:50 and 1:100, were also examined, but no further improvement was noted.

Also as evident from FIG. 5, sodium deoxycholate combined with dipotassium glycyrrhizinate at the ratio ranging from 1:1 to 1:100 gave an enhanced and sustained effect, with the ratio of 1:50 (Example 2-e) being the most effective.

Experiment 3

Figure 6:
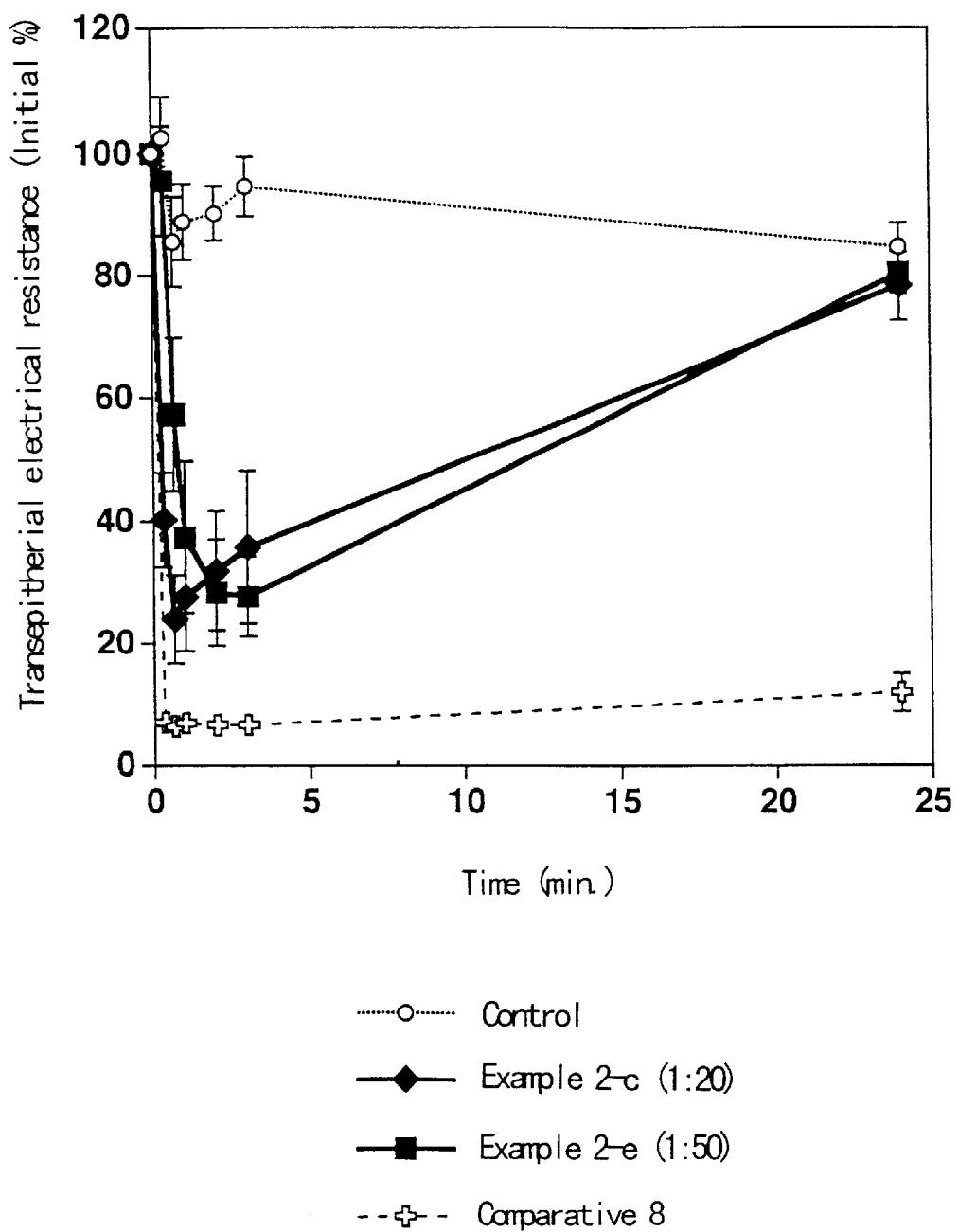
FIG. 6 is a graph showing the recovery of the transepitherial electrical resistance after the treatment with a solution of sodium caprate or sodium deoxycholate and dipotassium glycyrrhizinate.

The absorption enhancers prepared in Example 2, i.e., sodium caprate combined with dipotassium glycyrrhizinate at 1:20 (Example 2-c) and sodium deoxycholate combined with dipotassium glycyrrhizinate at 1:50 (Example 2-e) were subjected to the experiment in which the side of the top was replaced with Dulbecco's modified EAGLE medium (DMEM) (supplemented with 10% fetal calf serum) and allowed to stand with warming for 24 hours. The results are shown in FIG. 6.

The Caco-2 cell treated with the absorption enhancers of Example 2-c or Example 2-e was separated from the culture medium and then washed once with a phosphate buffer, and then made completely free from all solutions. Each 0.5 ml of a 0.05 mg/ml neutral red solution was added to each of the top side and the bottom side, and allowed to stand for 24 hours with warming. After allowing to stand with warming followed by removing the solution, the dye accumulated in the cell was extracted and examined for an absorbance in a standard manner. The results are shown in FIG. 7.

About 0.1 ml of a 0.4% trypan blue solution was added to the top side of a cell which had been treated and washed similarly, which was then allowed to stand for 1 to 2 minutes and then washed once with a phosphate buffer. The cell was placed together with a filter in 1.0 ml of an extraction solvent (0.5% $Na_2SO_4$: acetone=3:7) and treated ultrasonically and filtered to obtain a supernatant, which was measured at 560 nm. In this experiment, the volume of the extraction solvent was 1.0 ml, respectively.

In the experiment described above, a cytotoxic 0.2% sodium dodecylsulfate (Comparative 8)-treated group was also provided.

Figure 7:
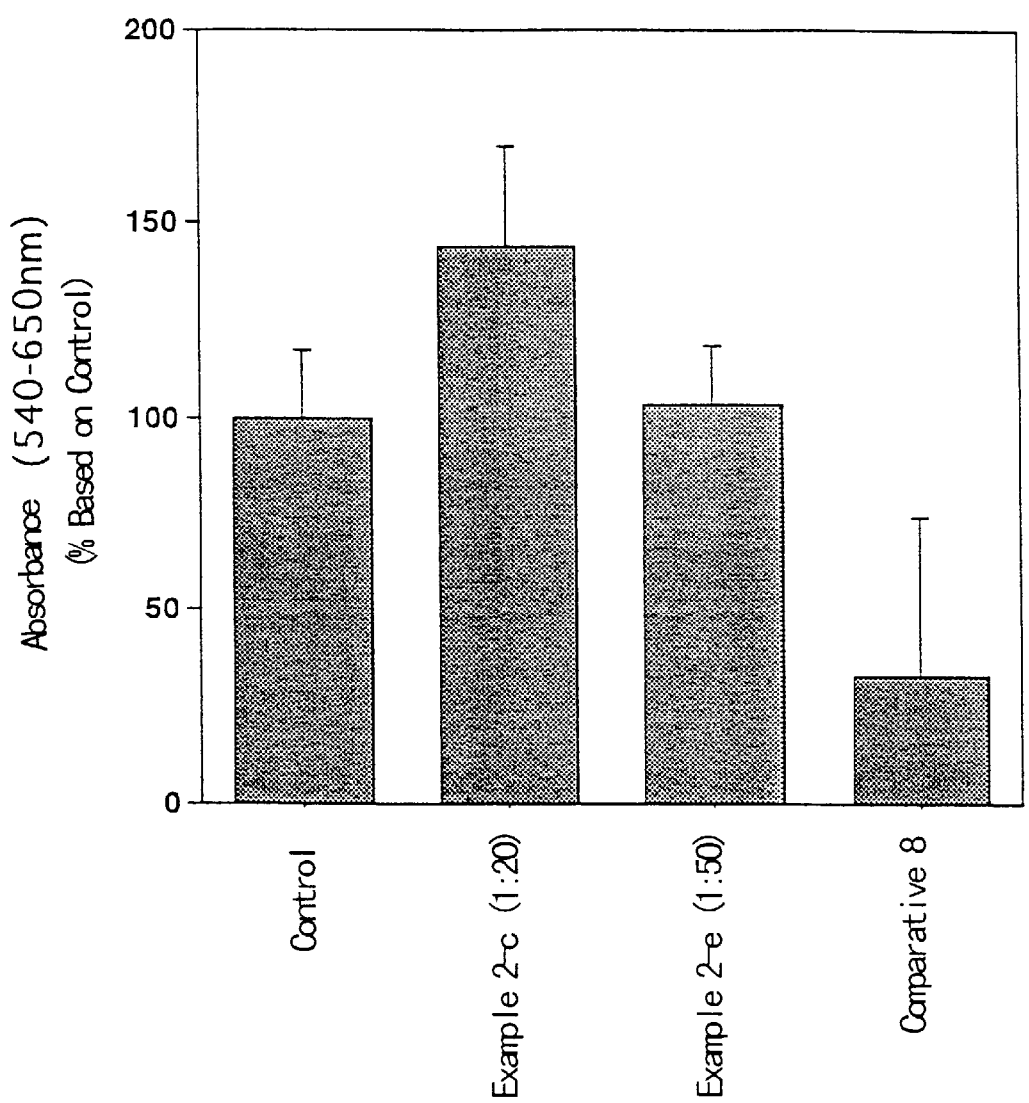
FIG. 7 is a graph showing the cell-stimulating activity determined by a neutral red method after the treatment with a solution of sodium caprate or sodium deoxycholate and dipotassium glycyrrhizinate.
Figure 8:
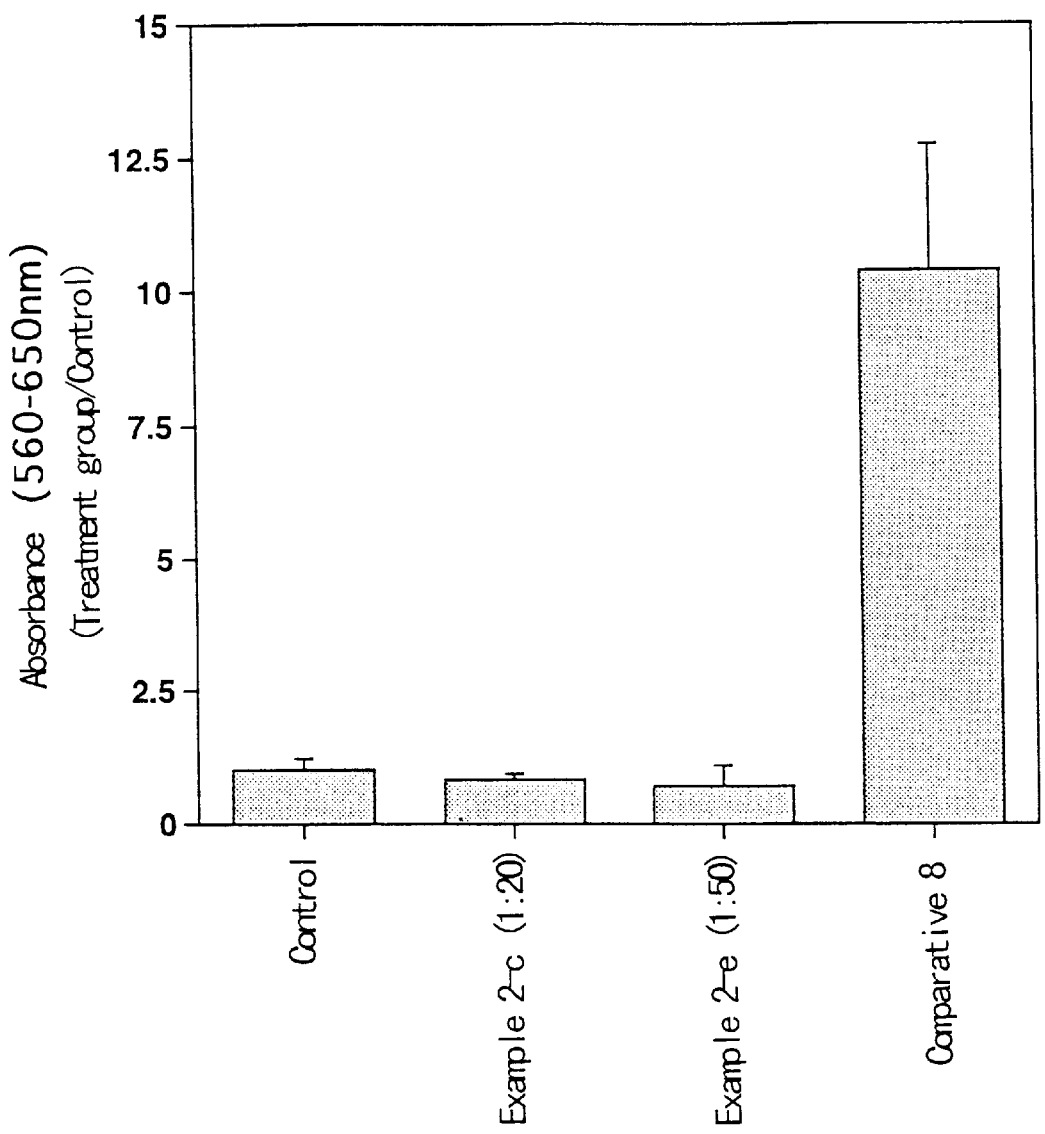
FIG. 8 is a graph showing the cell-stimulating activity determined by a trypan blue staining method after the treatment with a solution of sodium caprate or sodium deoxycholate and dipotassium glycyrrhizinate.

Both treatment groups exhibited a recovery of the TEER after 24 hours to the level similar to the control group as shown in FIG. 6, and the results were similar to those in the non-treatment group as shown in FIG. 7 and FIG. 8, revealing almost no cell-stimulating effect of any absorption enhancer under the conditions employed here.

Experiment 4

A absorption enhancer prepared in Example 2, comprising sodium caprate combined with dipotassium glycyrrhizinate at 1:20 (Example 2-c), was subjected to a Caco-2 monolayer permeability test. An agent allowed to permeate in the permeability test was fluorescein sodium (Sigma) or fluorescein isothiocyanate dextran 4000 (Sigma) dissolved in HBSS/CMF at a concentration of 0.1 mg/ml or 1.0 mg/ml.

In the Caco-2 monolayer permeability test, the pretreatment similar to that in the TEER test was performed and then only the top side was treated with a absorption enhancer for 20 minutes. The absorption enhancer was removed and washed once thoroughly with HBSS/CMF, and then HBSS/CMF including permeanator was added again to initiate the experiment.

Figure 9:
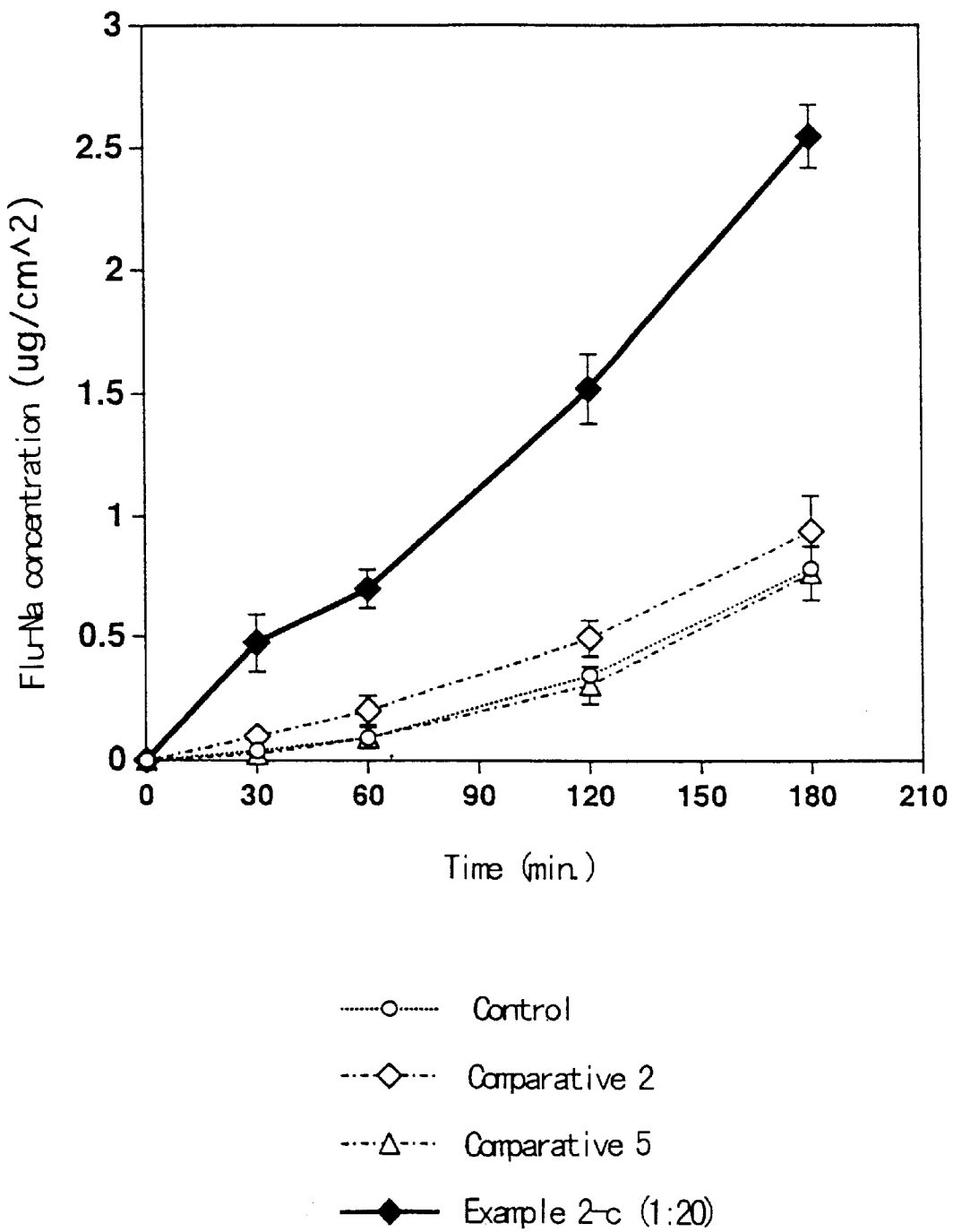
FIG. 9 is a graph showing the permeability of fluorescein sodium observed at the most effective ratio of dipotassium glycyrrhizinate and sodium caprate.
Figure 10:
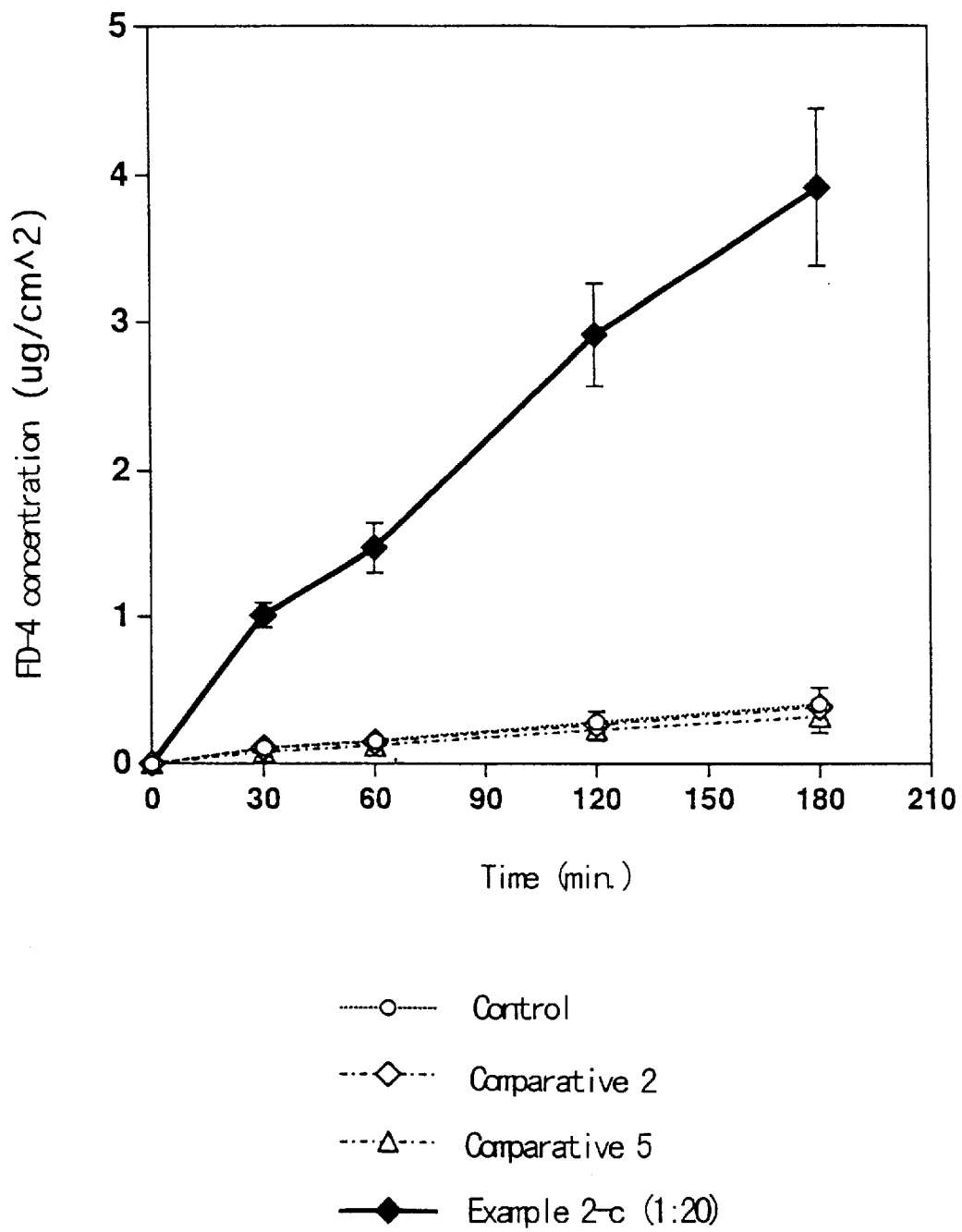
FIG. 10 is a graph showing the permeability of fluorescein isothiocyanate dextran 4000 observed at the most effective ratio of dipotassium glycyrrhizinate and sodium caprate.
Figure 11:
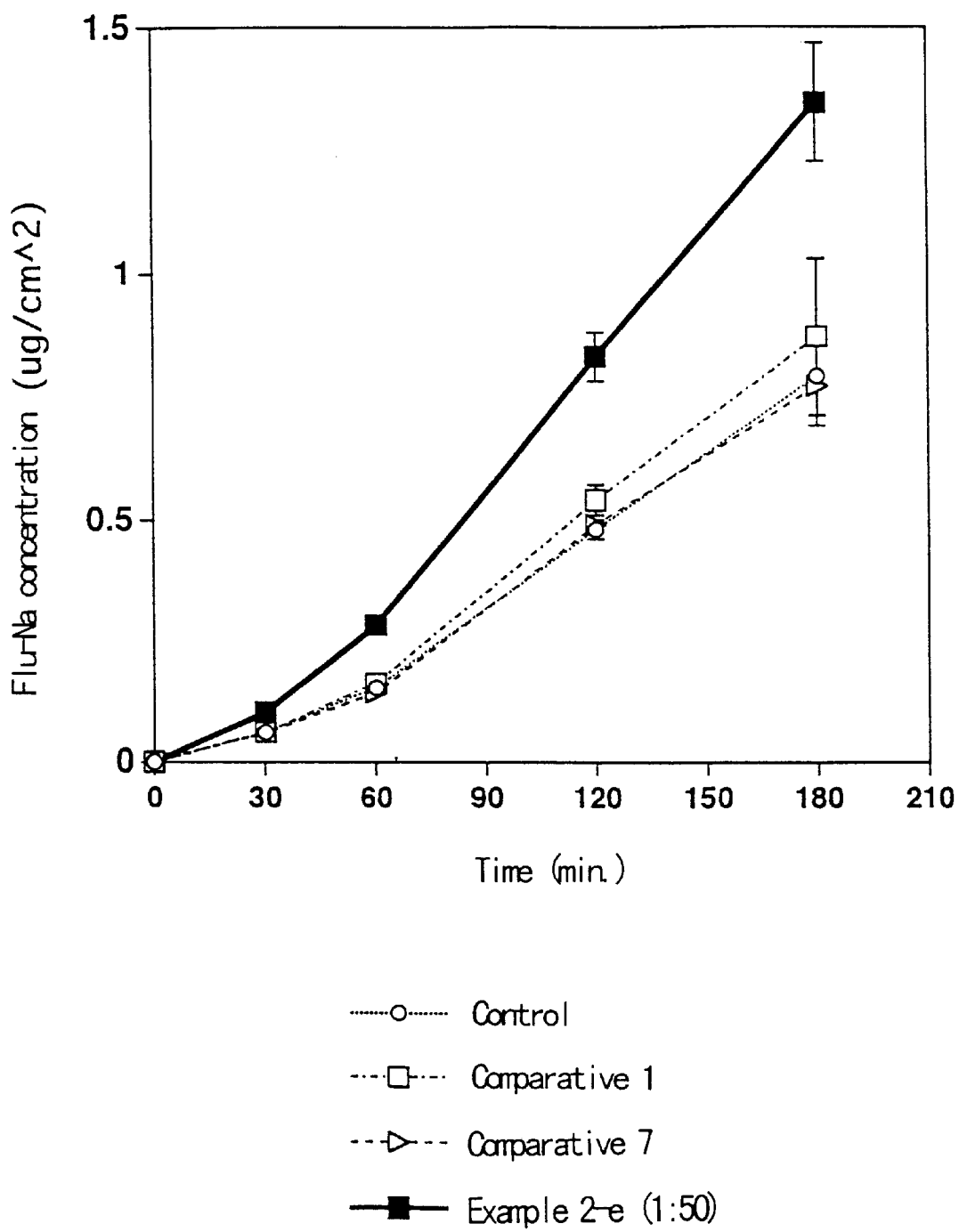
FIG. 11 is a graph showing the permeability of fluorescein sodium observed at the most effective ratio of dipotassium glycyrrhizinate and sodium deoxycholate.
Figure 12:
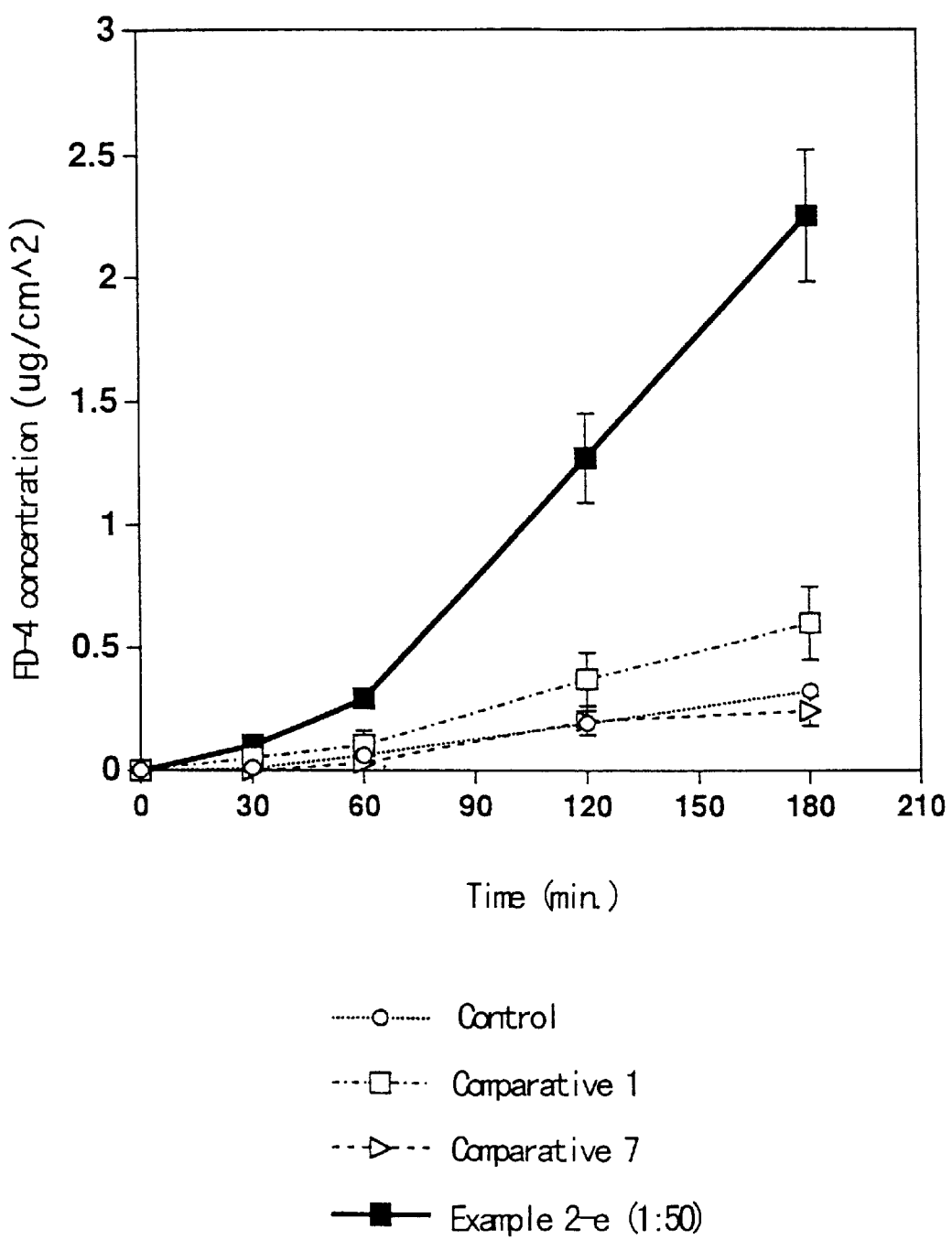
FIG. 12 is a graph showing the permeability of fluorescein isothiocyanate dextran 4000 observed at the most effective ratio of dipotassium glycyrrhizinate and sodium deoxycholate.

The results are shown in FIG. 9 and FIG. 10. The combination of sodium deoxycholate and dipotassium glycyrrhizinate at 1:50 was subjected to the permeability test using fluorescein sodium and fluorescein isothiocyanate dextran 4000. The results are shown in FIG. 11 and FIG. 12.

Experiment 5

A salmon calcitonin dissolved at 80 μg/ml in a solution of Example 2-c in a phosphate buffer (pH7) was administered at 2 ml/head to the large intestinal tract of an experimental animal (SD rat, 8 weeks old, male) under an anesthesia with ether to perform an absorption test. After administration, a heparinized blood was taken at a certain time interval under no anesthesia to determine a plasma concentration of calcium.

Figure 13:
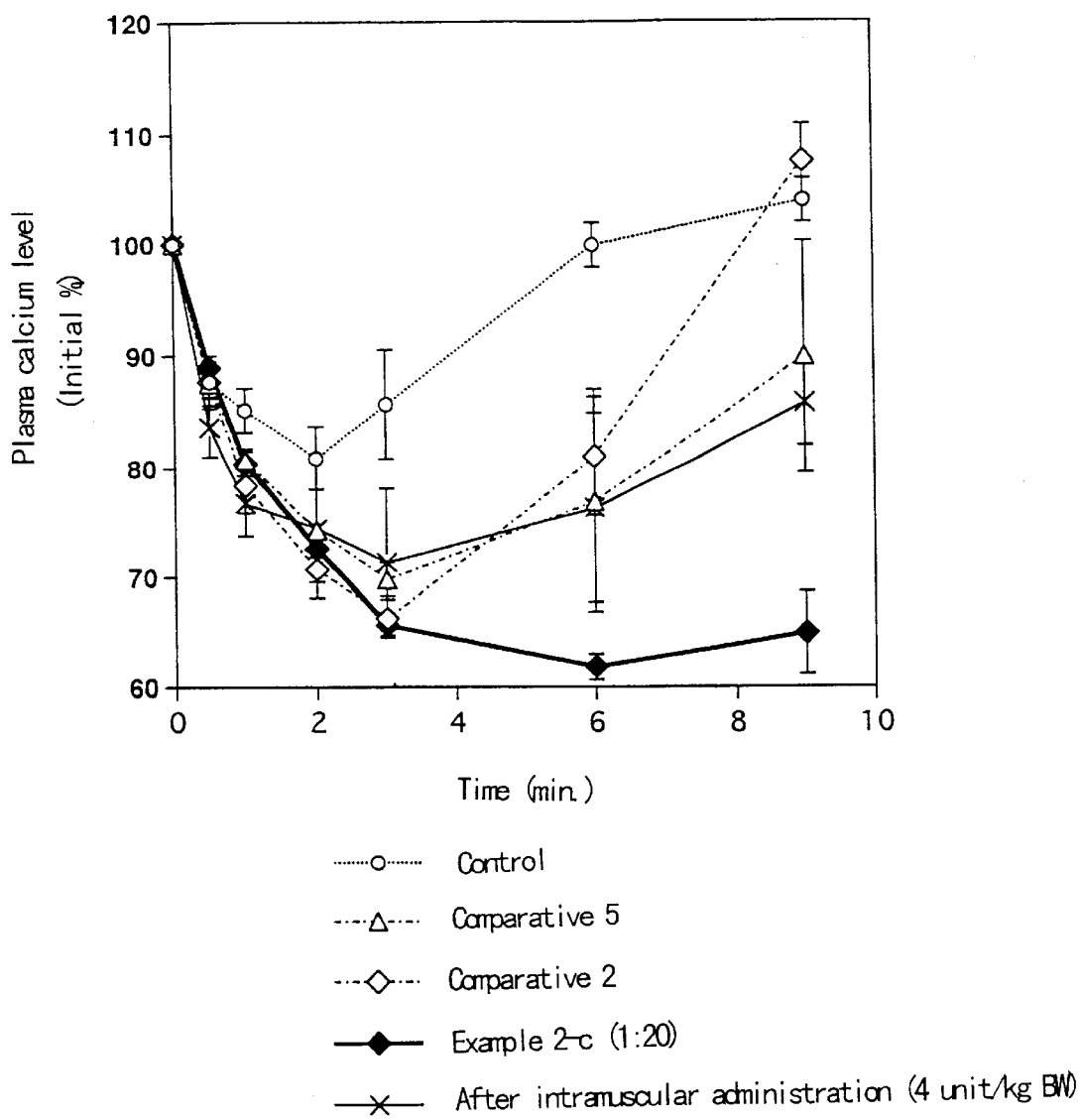
FIG. 13 is a graph showing the in vivo effect observed at the most effective ratio of dipotassium glycyrrhizinate and sodium caprate.

The results are shown in FIG. 13, which revealed that the absorption enhancer of Example 2-e exhibited a more enhanced and more sustained effect when compared with the effect of only one of the two constituents (Comparatives 2 and 5).

As described above, the present invention provide a absorption enhancer capable of sustaining the effect of the absorption enhancer and allowing an agent (especially a physiologically active peptide) to be absorbed more efficiently via a mucosa (especially a large intestine mucosa)

What is claimed is:

1. A transmucous absorption enhancer comprising a medium-chain fatty acid salt and a glycyrrhizic acid salt, wherein the ratio of said medium-chain fatty acid salt and said glycyrrhizic acid salt is 1:2 to 1:100.

2. A transmucous absorption enhancer according to claim 1 wherein said glycyrrhizic acid salt is a monoammonium glycyrrhizinate or an alkaline metal glycyrrhizinate.

3. A transmucous absorption enhancer according to claim 1 wherein said medium-chain fatty acid salt is an alkaline metal salt of capric acid, caprylic acid or caproic acid.

4. A transmucous absorption enhancer comprising a bile acid salt and a glycyrrhizic acid salt, wherein the ratio of said bile acid salt and said glycyrrhizic acid salt is 1:1 to 1:100.

5. A transmucous absorption enhancer according to claim 4 wherein said glycyrrhizic acid salt is a monoammonium glycyrrhizinate or an alkaline metal glycyrrhizinate.

6. A transmucous absorption enhancer according to claim 4 wherein said bile acid salt is sodium cholate, sodium glycocholate, sodium taurocholate, sodium deoxycholate or sodium cenodeoxycholate.

* * * * *